Figure 1:
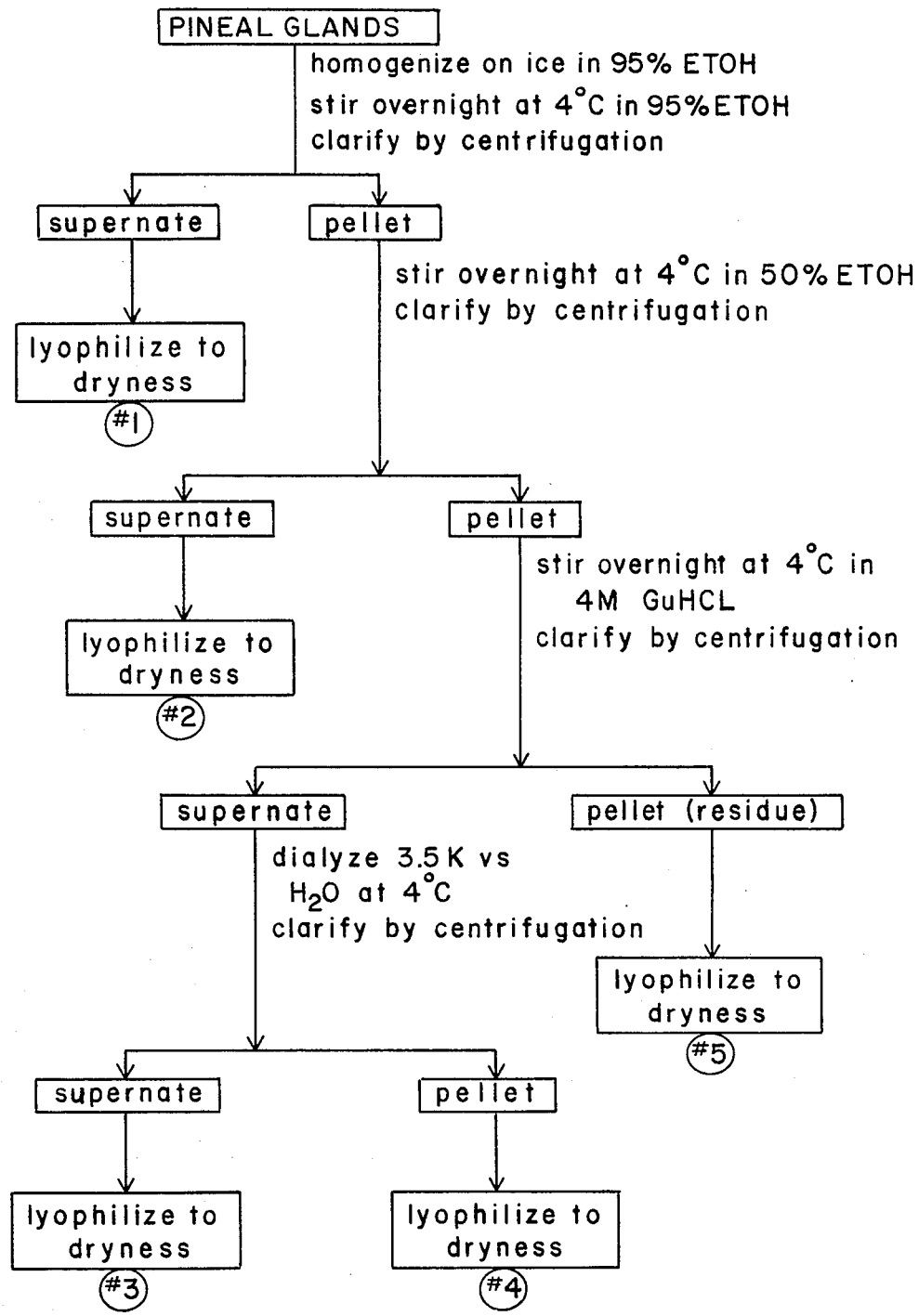

United States Patent [19]

Walton

[11] Patent Number: 4,702,912

[45] Date of Patent: Oct. 27, 1987

[54] BIOACTIVE COMPOSITIONS AFFECTING HUMAN SKIN TISSUE

[76] Inventor: Alan G. Walton, 17 Walnut La., Weston, Conn. 06883

[21] Appl. No.: 599,881

[22] Filed: Apr. 13, 1984

[51] Int. Cl.⁴ .................. A61K 7/42; A61K 35/12
[52] U.S. Cl. .................................. 424/95; 424/59; 514/844; 514/846; 514/847; 514/937
[58] Field of Search .................................. 424/95

[56] References Cited

U.S. PATENT DOCUMENTS 2,066,302  12/1936  Reichel .................................. 424/95

FOREIGN PATENT DOCUMENTS

| 772997 | 1/1972 | Belgium | 424/95 |
| 601269 | 8/1934 | Fed. Rep. of Germany | 424/95 |
| 634560 | 8/1936 | Fed. Rep. of Germany | 424/95 |
| 750730 | 5/1933 | France | 424/95 |
| 1022719 | 12/1952 | France | 424/95 |
| 1390184 | 1/1965 | France | 424/95 |
| 938241 | 10/1963 | United Kingdom | 424/95 |

OTHER PUBLICATIONS

Harry, 1962, The Principles and Practice of Modern Cosmetics, Modern Cosmeticology, vol. I, pp. 20 to 22.

Primary Examiner—Dale R. Ore
Attorney, Agent, or Firm—Thomas J. Monahan

[57] ABSTRACT

Compositions which affect cell metabolism of human skin cells are described. The compositions are purified bovine pineal gland extracts which selectively slow down cellular proteoglycan biosynthesis associated with the production of extracellular matrices without significantly affecting other cellular metabolic activities. These compositions can be used in cosmetics for the maintenance and improvement of skin structure and texture.

18 Claims, 2 Drawing Figures

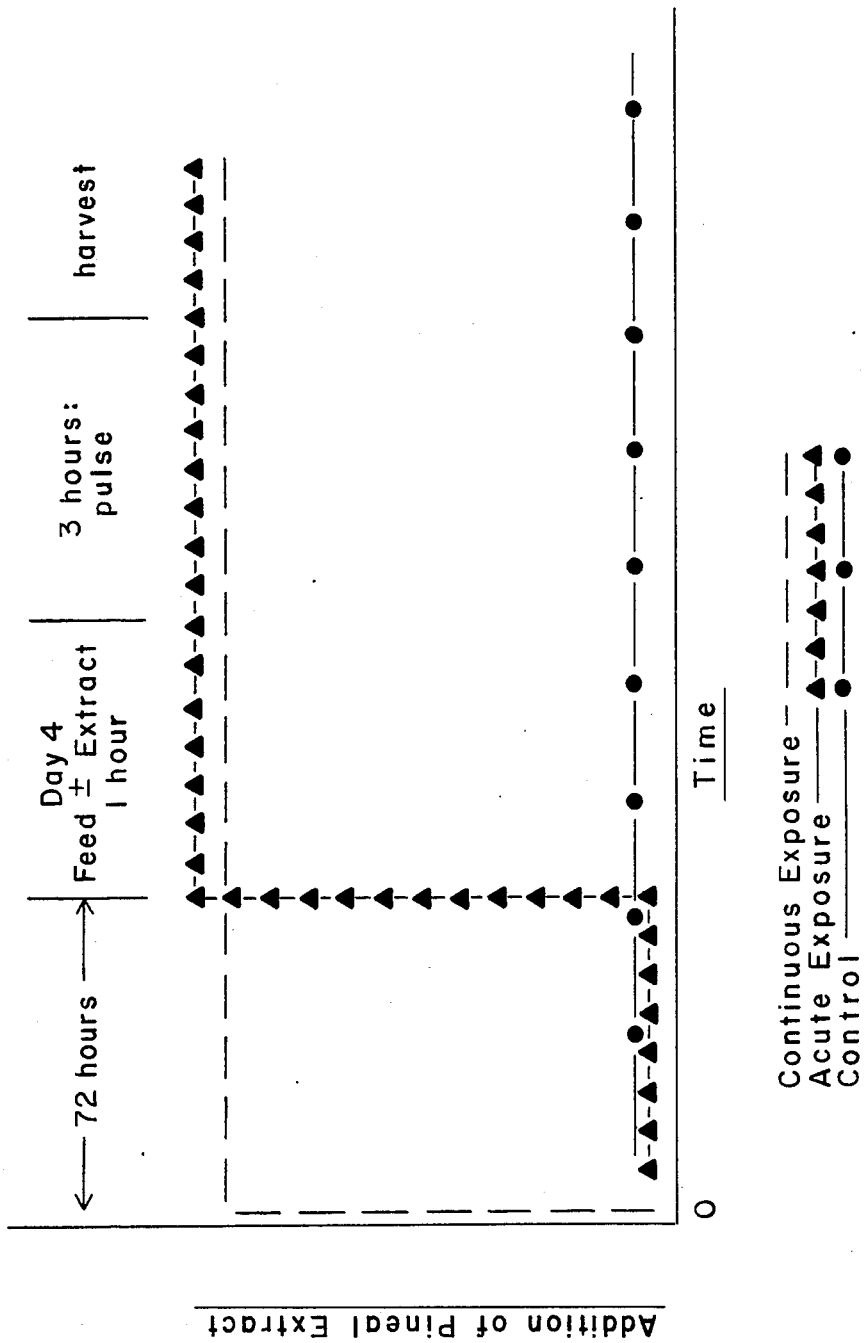

BIOACTIVE COMPOSITIONS AFFECTING HUMAN SKIN TISSUE

The invention herein described relates to various compositions which affect metabolic activities of cells of human skin tissue. Bovine pineal glands are extracted and separated into several purified fractions. Results from tissue culture bioassay systems involving embryonic chick mesenchymal cells and human skin fibroblasts demonstrate that purified pineal gland extracts selectively inhibit cellular proteoglycan biosynthesis. These compositions do not significantly affect cellular biochemical activities other than proteoglycan biosynthesis. The synthesis of these macromolecules is associated with the shape, resiliency, and texture of tissue throughout the aging process. The compositions of the invention are useful in cosmetic preparations for the maintenance and improvement of skin structure and texture.

By way of background, the pineal gland is a small structure located in the brain on the upper surface of the thalamus between the two halves of the cerebral cortex. This gland has known endocrine activity. It is clear from various animal investigations and information related to human disease, that the pineal gland plays a role in the process of aging. For example, if the pineal gland is absent or malfunctioning, aging is accelerated. The pineal gland is also known to be sensitive to light and to secrete the hormone melatonin. Recent evidence suggests that melatonin interacts with the brain and the pituitary gland in the regulation of reproductive hormones. Various effects such as early childhood restraint on sexual maturation and sleep regulation have been associated with pineal activity. The multifaceted functions of the pineal gland are complex and not well understood.

There are various theories regarding the diverse and complex aspects of the process of aging. It is known that aging involves significant deteriorative changes ranging from the molecular and cellular levels to the tissue and organ levels. The aging process is controlled by an organism's genetic apparatus and observed aging changes are effected by various mechanisms. Once the complexities of the genetic basis of aging are elucidated, it is not unlikely that results from research involving recent genetic engineering technologies, most notably recombinant DNA processes, will permit control of aging. However, until such ultimate genetic control is achieved, it is desirable to attempt to ameliorate the deteriorative effects of aging.

Among the more readily observed effects of aging are changes in skin structure and texture. Such modifications are variously referred to as wrinkling or leathering of skin and are routinely accompanied by decreases in skin moisturization properties. These skin changes with age are exacerbated by various environmental factors such as excessive exposure to the elements, certain diseases, various pharmaceuticals and other elements. Psychological factors, for example, can accelerate the aging process. Changes in skin texture and structure are currently regarded as irreversible. However, these changes are at least partially mitigatable by use of various natural and synthetic skin creams and oils or other topical preparations in concert with alteration of environmental factors whenever possible. There are numerous commercial products available for the cosmetic treatment of skin which are designed to ameliorate dryness or other effects of aging.

The connective tissue of humans consists of various important structural materials, such as collagen, elastin, keratin, proteoglycans, and various other minor components. Keratin is a tough, fibrous proteinaceous material that forms the outer layer of epidermal structures such as hair and nails. Elastin is the albuminoid base of elastic tissue such as tendons, ligaments and cartilage. Collagen is a fibrous protein constituent of bone, cartilage, and connective tissue which imparts mechanical strength. Proteoglycans are large complex macromolecules, consisting of proteinaceous and polysaccharide material, which are primarily responsible for maintaining water content in the extracellular matrix of connective tissue. These macromolecules are involved in the determination of tissue shape, resiliency, and texture. Although their relative amounts vary considerably, collagen and proteoglycans are widely distributed in human tissues. Collagen is used in cosmetic preparations and for the treatment of acne.

In light of the foregoing discussion of selected aspects of the process of aging, and more specifically to elements of the aging of skin tissue, development of compositions useful for the cosmetic treatment of skin are highly desirable. Accordingly, an object of this invention is to provide new and useful chemical compositions which are effective for the maintenance of skin structure and texture. A further object is to provide a method for the extraction and concentration of said active compositions from bovine pineal glands. Yet another object is to provide compositions which selectively slow down cellular metabolism. These and further objects are manifest in the following description and particularly delineated in the appended claims.

The invention herein described involves the extraction of bovine pineal glands and the subsequent evaluation of several extraction factions by use of two bioassay systems. Extracts from bovine pineal glands have been unexpectedly discovered having specific biochemical activity. Pineal glands are homogenized in 95% ethyl alcohol, are further extracted with 95% ethyl alcohol by continuous stirring overnight, and are centifuged. The supernate obtained is lyophilized to dryness (Fraction No. 1). The centrifuged pellet is then extracted with 50% ethanol by stirring overnight and centrifuged. This supernate is lyophilized to dryness (Fraction No. 2) and the resultant pellet is extracted with 4M guanidinium chloride (GuHCl) and again clarified by centrifugation. The pellet thus obtained from this centrifugation is lyophilized to dryness (Fraction No. 5) and the supernate is dialyzed against water and clarified by centrifugation. The resultant supernate is lyophilized to dryness (Fraction No. 3) and the pellet is also lyophilized to dryness (Fraction No. 4). Fractions Nos. 3 and 5 are found to be especially active when evaluated by bioassay systems and are preferred embodiments of the invention. The isolated fractions of dry material are taken up in Eagle's Minimal Essential Medium for tissue culture in preparation for bioassay. Any insoluble material is separated by centrifugation and discarded.

An embryonic chick limb mesenchymal cell culture system serves as one of the bioassays of the invention. This system is designed to evaluate cell differentiation. This bioassay system assesses the differentiation of embryonic mesenchymal cells into chondrocytes which function to produce cartilage. The procedure used in the chick limb mesenchymal cell assay is described in the literature and involves staining and visual evaluation of the number of chondrogenic cells in culture [Caplan, A. E., Exp. Cell. Res. 62: 341-355 (1970)]; Schacter, L. P., Exp. Cell. Res. 63: 19-32 (1970)]. This assay also provides information on the biosynthesis of cartilage-specific extracellular matrix in such cell cultures. Thus, this bioassay system is capable of evaluating differentiation and proteoglycan biosynthesis. Differentiation can be evaluated by observing cell morphology as cells transform from undifferentiated mesenchymal cells into chondrocytes, or cartilage-producing cells. Proteoglycan biosynthetic activity is evaluated by measuring the rate of incorporation of radio-labelled sulfate into cartilage proteoglycans.

A cell culture system involving the use of human foreskin fibroblasts is also used as a bioassay to evaluate compositions of the invention. Radio-labelled proline is used to estimate protein synthesis in fibroblast tissue culture cells and radio-labelled sulfate is used to measure proteoglycan biosynthesis following exposure of cultures to pineal extracts of the invention. Human skin fibroblast cells are grown under standard aseptic tissue culture conditions in petri plates containing nutrient medium. Cells in log phase growth are inoculated and allowed to grow for three days. After this initial incubation period, pineal gland extracts of the invention are added to several cultures which are then incubated for three days, re-fed with fresh medium containing pineal extracts and exposed for three hours to radio-labelled proline and sulfate. Cells are then harvested and washed; protein, proteoglycan, and total cell density DNA are then determined. Cultures thus prepared and treated are referred to as continuous-exposure cultures. Other cultures inoculated in log phase growth are re-fed with fresh medium containing pineal extracts, exposed for three hours to radioactive protein and sulfate, harvested, washed, and assayed for protein synthesis, cell density, proteoglycan synthesis, and total DNA. Cultures thus prepared and treated are referred to as acute-exposure cultures. Control cultures are similarly treated and assayed except that they are not exposed to the pineal gland extracts of the invention.

Pineal gland extract No. 5 is particularly found to inhibit both the extent of differentiation of mesenchymal cells into chondrocytes and the biosynthesis of proteoglycans as determined by use of the chick limb mesenchymal cell bioassay system. Fraction No. 5 is also found to specifically inhibit proteoglycan biosynthesis as evaluated by the fibroblast tissue culture bioassay system. The composition of this pineal gland extract is an especially preferred embodiment of the invention.

Compositions of the invention can conveniently be formulated in solid or liquid form, either singularly or in combination thereof, in various bases (i.e., water, various alcohols or other organic solvents, lipids, creams, various emulsions or the like, or mixtures of said bases), as cosmetically-acceptable emollients for topical application to skin. Such cosmetic preparations are useful for the maintenance and improvement of skin structure and texture. The active ingredient(s) is/are present at concentrations ranging from approximately 1 $\mu$g to 100 mg of dry material per ml or cc of the cosmetic preparation.

The following Examples further serve to illustrate the invention and are not intended to be limitative thereof.

EXAMPLE 1

Procedure for the Extraction of Bovine Pineal Glands

Bovine pineal glands are extracted to provide five different fractions which are subsequently tested for activity by the bioassay systems of the invention. A sample of bovine pineal glands is homogenized on ice in 95% ethyl alcohol, stirred overnight at approximately 4° C., and then clarified by centrifugation. The supernate thus obtained is lyophilized to dryness giving Fraction No. 1 and the centrifuged pellet is stirred overnight at approximately 4° C. in 50% ethyl alcohol. The resultant supernate is lyophilized to dryness giving Fraction No. 2 and the centrifuged pellet is then stirred overnight at approximately 4° C. in 4M GuHCl and clarified by centrifugation. The pellet residue thus obtained is lyophilized to dryness and identified as Fraction No. 5. The supernate obtained from the above GuHCl extraction step is dialyzed against distilled water at approximately 4° C. in dialysis tubing with a molecular weight cut-off of 3500 and clarified by centrifugation. The supernate is then lyophilized to dryness giving Fraction No. 3. The pellet residue is also lyophilized to dryness giving Fraction No. 4. Thus, Fraction No. 1 is a 95% ethanol extract of pineal glands; Fraction No. 2 is a 50% ethanol extract; Fraction No. 3 is a 4M GuHCl-soluble, water-soluble extract; Fraction No. 4 is a 4M GuHCl-soluble, water-insoluble extract; and Fraction No. 5 is a 4M GuHCl residue. The extraction procedure is further described in diagramatic form in FIG. 1. Yield information obtained from the extraction of 200 bovine pineal glands (frozen from "Pel-Freeze") according to this procedure is presented in Table 1.

TABLE 1

Yields Obtained from the Extraction of 200 Bovine Pineal Glands (27.94 grams net weight) According to the Procedure of Example 1

| Fraction No. | % of Starting Wet Weight (27.94 grams) | % of Extracted Weight |
| --- | --- | --- |
| #1 | 3.6 | 4.9 (1.0 gm) |
| #2 | 3.2 | 4.4 (0.9 gm) |
| #3 | 0.24 | 0.33 (0.066 gm) |
| #4 | 2.3 | 3.2 (0.65 gm) |
| #5 | 62.7 | 87.0 (17.5 gm) |
| | 72.0% of Starting Wet Weight is Extracted and Recovered | 20.116 grams of extracted material |

EXAMPLE 2

BIOASSAY OF PINEAL GLAND EXTRACTS USING EMBRYONIC CHICK LIMB MESENCHYMAL CELL CULTURES

Following the procedure of Example 1, five different fractions are obtained and several fractions are subjected to a bioassay using chick limb mesenchymal cell cultures. This system is designed to evaluate the effect of the pineal gland extracts on the differentiation of embryonic mesenchymal cells into chondrocytes and the ability of differentiated chondrocytes to produce cartilage. Pineal extracts are found to specifically retard proteoglycan biosynthesis at concentrations which do not substantially affect other cellular bioactivities. Proteoglycans are extracellular moieties which represent the major water-structuring macromolecules found in matrices around chondrocytes which function to provide tissues such as cartilage or skin with resiliency and texture. The dry fractions obtained by the process of Example 1 are taken up in Eagle's Minimal Essential Medium (MEM) for tissue culture. MEM is a commercially available balanced salt solution. Any material which is insoluble in this solution is centrifuged and removed.

Limb mesenchymal cells are liberated from stage 24 check embryos and placed into culture by procedures known in the art [Caplan, A. I., Exp. Cell. Res. 62: 341–355 (1970)].

Proteoglycan biosynthesis is determined by measuring incorporation of radio-labelled sulfate ($^{35}$S-SO$_4$). Protein biosynthesis is determined by measuring incorporation of radio-labelled proline. ($^3$H-proline), and DNA biosynthesis is determined by measuring incorporation of radio-labelled thymidine ($^3$H-thymidine). The production of cartilage is determined by visual examination of cell cultures [Hascall, V. C., Oegema, T. R., Brown, M., and Caplan, A. I., J. Biol. Chem. 251: 3511–3519 (1976)].

In this bioassay, chick limb mesenchymal cell cultures are grown in the presence of pineal gland extracts of the invention (Fractions Nos. 1–5) at various concentrations, with the highest concentration tested being in excess of 2 mg of dry extract material per ml of culture medium. Extracts Nos. 3 and 5 are found to be effective at concentrations of approximately 0.1 to 0.5 mg of dry extract material per ml of culture medium. Optimum results are obtained at a concentration of 0.5 mg of dry material per ml of culture medium.

The pineal gland extract identified as Fraction No. 5 is found to be heat sensitive. Activity of this fraction is destroyed after exposure to a temperature of 80° C. for one hour.

Results of this bioassay are presented in Table 2. These data show that compositions of the invention slow down differentiation of chick limb mesenchymal cells while affecting basic aspects of cell metabolism to a lesser degree.

(MEM) for tissue culture and any insoluble material is removed by centrifugation and discarded. In all experiments evaluating the effects of exposure to pineal gland extracts, protein systhesis is estimated by use of $^3$H-proline (2 μCi/ml) and proteoglycan synthesis is determined by use of $^{35}$S-SO$_4$ (10 μCi/ml).

To initiate the cell line used for the bioassay of the pineal gland extracts of the invention, a human foreskin sample is first obtained from a hospital patient. A tissue culture of this sample is then developed and subsequently maintained on Eagle's MEM supplemented with 10% fetal calf serum (FCS). The tissue culture is frozen at the second passage (58 days in culture), reconstituted, and passed two additional times before cells are harvested for use in the present bioassay system. One hundred eight expanded dishes (60×15 mm) are inoculated at a concentration of 1.53×10$^5$ cells/dish (69 cells/mm$^2$). Dish cultures are fed with five ml of fresh culture medium three times per week. These expanded dish cultures serve as stock cultures of fibroblast cells and are used to inoculate petri plates after seven (7) days of growth. Cells are actively metabolizing at this time.

The bioassay petri plates are inoculated with cells from the expanded dish culture as a described above. Each petri plate contains three (3) ml of test culture medium. The day of inoculation is referred to as Time Zero (0). Some plates inoculated at Time Zero contain nutrient medium supplemented with pineal extract (Continuous Exposure) and the remainder contain only Eagle's MEM with 10% FCS. Three (3) days after inoculation, all plates are re-fed with three (3) ml of test medium as follows: some with nutrient medium containing pineal extract (Acute Exposure cultures have pineal extract added for the first time, whereas Continuous Exposure cultures are re-fed with fresh medium supplemented with pineal extract); some with unsupplemented nutrient medium (Control cultures). Radio-labelled tracers are added to some of the Control, Acute and Continuous Exposure cultures to determine protein and

TABLE 2

Mesenchymal Cell Bioassay of Pineal Gland Extracts

| Treatment (Fraction #1) | Concentration of Extract (mg dry material/ ml culture medium) | Production of Cartilage | Proteoglycan Biosynthesis (% of Control) | Protein Biosynthesis (% of Control) | DNA Biosynthesis (% of Control) |
|---|---|---|---|---|---|
| #1* | 0.5 | like control | — | — | — |
| #2* | 0.5 | like control | — | — | — |
| #3* | 0.5 | inhibition of cartilage matrix deposition | 18 | 25 | — |
| #4* | 0.5 | like control | — | — | — |
| #5* | 0.5 | complete inhibition of cartilage matrix deposition | 2 | 13 | — |
| #5*** | 0.5 | almost complete inhibition | 29 | — | 62 |

*Cultures are exposed to pineal extracts from day 3 to day 6 of the experiment; on day 6 the radio-labelled tracer is added and quantitated after 3 hours of exposure.
**Data presented are the averages of experiments performed in triplicate.
***Cultures are exposed to pineal extracts from day 1 to day 8 of the experiment; on day 8 the radio-labelled tracer is added and quantitated after 3 hours of exposure.

EXAMPLE 3

BIOASSAY OF PINEAL GLAND EXTRACTS USING HUMAN FORESKIN FIBROBLAST CELL CULTURES

Following the procedure of Example 1, fractions #3 and #5 are obtained and subjected to a bioassay using human foreskin fibroblast cell cultures. The dry fractions are taken up in Eagle's Minimal Essential Medium proteoglycan synthesis. Radio-labelled proline ($^3$H proline at 2 μCi/ml) is added to estimate protein synthesis and radioactive sulfate ($^{35}$SO$_4$ at 10 μCi/ml) is used to estimate proteoglycan synthesis. All radio-labelled plates are first washed with sulfate-free medium. Unlabelled plates are used for the determination of DNA. After three hours of incubation at 37° C., all plates are harvested and the following data are obtained: total cell layer associated $^3H$ incorporation/3 hours; total cell layer associated $^{35}S$ incorporation/3 hours; and total DNA/plate. The experiment is performed with triplicate cultures. Accordingly, all measurements are made on three separate plates. The experimental procedure used in the fibroblast bioassay system is further described diagramatically in FIG. 2.

Harvest Procedure for Culture Medium and Radio-Labelled Sulfate Determination The harvesting of all radio-labelled tissue culture plates is performed on ice. Two ml of labelled-medium are removed from each culture and placed in a conical centrifuge tube for the sulfate incorporation assay. The remaining medium is discarded. The medium to be assayed is precipitated overnight in 70% ethyl alcohol [two (2) ml culture medium plus five (5) ml of absolute ethanol] and centrifuged at room temperature for ten (10) minutes at 1500 rpm. The supernate thus obtained is discarded; one (1) ml of 70% ethanol is added and the pellet is dispersed by shaking the centrifuge tube. The tube is then tightly capped, placed in a boiling water bath for one to two minutes, and removed from the bath as soon as the ethanol boils. The tube is then centrifuged at room temperature for ten (10) minutes at 1500 rpm. The supernate thus obtained is discarded. The above steps involving the addition of one (1) ml 70% ethanol, shaking, boiling, and centrifugation are then repeated twice. The resultant precipitate is solubilized overnight in two (2) ml of Nuclear Chicago Solvent (NCS). One-half (0.5) ml of NCS solubilized precipitate is placed in a glass scintillation vial, eight (8) ml of omnifluor is added, and the radioactivity of the sample is counted.

Harvest and Counting Procedures for Radio-Labelled Cells

Petri plates are washed twice with three (3) ml of cold calcium-and-magnesium-free Basic Saline Solution (BSS). Three (3) ml of cold 10% trichloracetic acid (TCA) is added and the liquid preparation is allowed to sit for thirty (30) minutes. The TCA is removed and discarded. An additional three (3) ml of cold 10% TCA is added, removed and discarded. Two (2) ml of cold calcium-and-magnesium-free BSS is then added. Cell are then scraped from the petri plate with a spatula and the cell layer is transferred to a fifteen (15) ml conical plastic centrifuge tube where the material is cold centrifuged for fifteen (15) minutes at 1500 rpm. The supernate is discarded and the pellet is transferred to a twenty (20) ml glass scintillation vial. Two (2) ml of undiluted NCS is then added and incubated overnight at room temperature. Eight (8) ml of omnifluor is then added and the radioactivity of the sample is counted.

Harvest and DNA Determination Procedure for Unlabelled Cells

The culture medium is removed and discarded. Plates are washed once with calcium-and-magnesium-free Basic Saline Solution (BSS). Five (5) ml of 0.025% pronase B is added and incubated for fifteen (15) minutes at 37° C. The cell suspension from each plate is then transferred to a centrifuge tube and centrifuged at room temperature for fifteen (15) minutes at 1500 rpm. The supernate is discarded and the cells are then resuspended in five (5) ml of culture medium. One (1) ml of this cell suspension is counted to determine cell concentration using an electronic Coulter Counter. The remaining four (4) ml of cell suspension is cold centrifuged for fifteen (15) minutes at 1500 rpm, and the supernate is removed and discarded. Cells are washed once with 0.15M cold NaCl and then cold centrifuged for fifteen (15) minutes at 1500 rpm. The supernate is discarded and the cell pellet is frozen prior to the determination of DNA.

To each frozen cell sample prepared as described above is added 0.25 ml of cold 1M trichloroacetic acid (TCA). Cells are disrupted by sonication (three times at ten second intervals). The probe is chilled between each sonication treatment. Two-tenths of a ml of sonicated cell material is placed in a centrifuge tube and centrifuged for ten (10) minutes at 15,000 rpm. The resultant supernate is decanted and discarded. One (1) ml of cold 95% ethanol is added to the cell material which is then centrifuged for ten (10) minutes at 15,000 rpm. The supernate is decanted and discarded. The sample is air dried at room temperature. To each sample and standard is added 0.1 ml of freshly prepared diaminobenzoic acid, DABA [300 mg/ml; prepared by adding 450 μg charcoal to 900 μg DABA, centrifuging at 3,000 rpm for ten (10 minutes; then centrifuging at 10,000 rpm for ome (1) minute in a Beckman Microfuge B; and filtering material through Whatman No. 1 filter paper]. Samples are incubated thirty (30) minutes at 60° C. To each sample is added 1.4 ml of 1M HCl and samples are read in an Aminco spectrophotometer with filters [primary—110:812 (405) plus 7.51 glass; secondary—110-822-58 (green)].

Results of the fibroblast bioassay of pineal gland extracts are presented in Table 3. These data show that pineal extracts of the invention significantly inhibit proteolycan biosynthesis (i.e., 60% inhibition) while only slightly affecting other cellular activities at preferred concentrations.

TABLE 3

| | Human Foreskin Fibroblast Bioassay of Pineal Gland Extracts | | | | | | |
|---|---|---|---|---|---|---|---|
| Treatment | Concentration of Extract | Radioactivity (DPM/$10^6$ cells)* | | Protein Synthesis | Proteoglycan Synthesis | DNA Content | |
| Fraction #/ Exposure | (μg dry material/ ml culture medium) | $^3H$ | $^{35}S$ | (% of Control) | (% of Control) | μg DNA/$10^6$ Cells | % of Control |
| #3 Control | 100 | 90977 | 47015 | 100.0 | 100.0 | 3.696 | 100.0 |
| #3 Continuous | 100 | 75059 | 18402 | 82.5 | 39.1 | 3.894 | 105.4 |
| #3 Acute | 100 | 75757 | 21232 | 83.3 | 45.2 | 3.884 | 105.1 |
| #3 Control | 10 | 87790 | 43789 | 100.0 | 100.0 | 3.636 | 100.0 |
| #3 Continuous | 10 | 82683 | 35022 | 94.2 | 80.0 | 3.574 | 98.3 |
| #3 Acute | 10 | 86531 | 35157 | 98.6 | 80.3 | 3.476 | 95.6 |
| #4 Control | 100 | 82440 | 37400 | 100.0 | 100.0 | 3.711 | 100.0 |
| #4 Continuous | 100 | 82050 | 22123 | 99.5 | 59.1 | 3.391 | 91.4 |
| #4 Acute | 100 | 69524 | 18064 | 84.3 | 48.3 | 3.685 | 99.3 |
| #4 Control | 10 | 90140 | 45426 | 100.0 | 100.0 | 3.752 | 100.0 |
| #4 Continuous | 10 | 79621 | 32030 | 88.3 | 70.5 | 3.962 | 105.6 |

TABLE 3-continued

| | Human Foreskin Fibroblast Bioassay of Pineal Gland Extracts | | | | | | |
|---|---|---|---|---|---|---|---|
| Treatment | Concentration of Extract | Radioactivity (DPM/$10^6$ cells)* | | Protein Synthesis | Proteoglycan Synthesis | DNA Content | |
| Fraction #/ Exposure | (μg dry material/ ml culture medium) | $^3$H | $^{35}$S | (% of Control) | (% of Control) | μg DNA/$10^6$ Cells | % of Control |
| #4 Acute | 10 | 88587 | 38292 | 98.3 | 84.3 | 3.984 | 106.2 |
| #5 Control | 100 | 79566 | 39564 | 100.0 | 100.0 | 3.491 | 100.0 |
| #5 Continuous | 100 | 64224 | 16225 | 80.7 | 41.0 | 3.267 | 93.6 |
| #5 Acute | 100 | 71111 | 19570 | 89.4 | 49.5 | 3.913 | 112.1 |
| #5 Control | 10 | 71447 | 34352 | 100.0 | 100.0 | 3.095 | 100.0 |
| #5 Continuous | 10 | 68313 | 33134 | 95.6 | 96.4 | 3.104 | 100.3 |
| #5 Acute | 10 | 72434 | 32604 | 101.4 | 94.9 | 3.387 | 109.4 |

*Numbers represent the respective means of experiments performed in triplicate.

What is claimed is:

1. A method for the preparation of bioactive compositions comprising the extraction steps performed at a cold temperature of:
    (a) homogenizing bovine; pineal glands in 95% ethanol, stirring said homogenate for a period of time to essentially complete the extraction, centrifuging said material, separating said resultant supernate and lyophilizing same to dryness (Fraction No. 1);
    (b) stirring said centrifugate of step (a) in 50% ethanol for a period of time to essentially complete the extraction, centrifuging, separating said resultant supernate and lyophilizing same to dryness (Fraction No. 2);
    (c) stirring said centrifugate of step (b) in 4M guanidine hydrochloride for a period of time to essentially complete the extraction, centrifuging, separating said resultant centrifugate and lyophilizing same to dryness (Fraction No. 5);
    (d) dialyzing said supernate of step (c) against water, centrifuging, separating said resultant supernate, and lyophilizing same to dryness (Fraction No. 3);
    (e) lyophilizing the centrifugate of step (d) to dryness (Fraction No. 4).

2. A method according to claim 1 wherein said period of stirring is overnight.

3. A method according to claim 2 wherein said cold temperature of the process of preparation is approximately 4° C.

4. A method according to claim 3 wherein and said homogenizing is done on ice.

5. A method for the preparation of biologically active compositions comprising the extraction steps performed at a cold temperature of:
    (a) homogenizing bovine pineal glands in 95% ethanol, stirring said homogenate for a period of time to essentially complete the extraction, and centrifuging said material;
    (b) stirring said centrifugate of step (a) in 50% ethanol for a period of time to essentially complete the extraction, and centrifuging,
    (c) stirring said centrifugate of step (b) in 4M guanidine hydrochloride for a period of time to essentially complete the extraction, centrifuging, separating said resultant centrifugate and lyophilizing same to dryness (Fraction No. 5).

6. A method according to claim 5 wherein said period of stirring is overnight, said cold temperature of the process of preparation is approximately 0°-4° C.

7. A method according to claim 5 wherein there is dialyzing of said supernate of step (c) against water, centrifuging, separating said resultant supernate and lyophilizing same to dryness (Fraction No. 3).

8. A method according to claim 7 wherein said period of stirring is overnight, and said cold temperature of the process of preparation is approximately 0°-4° C.

9. A method according to claim 7 wherein there is lyophilizing of the centrifugate of step (d) to dryness (Fraction No. 4).

10. A method according to claim 9 wherein said period of stirring is overnight and said cold temperature of the process of preparation is approximately 0°-4° C.

11. A biologically active cosmetic composition for the maintenance and improvement of skin structure and texture comprising from 1 μg to 100 mg of dry bovine pineal glands extract material per ml or cc of cosmetically-acceptable liquid solution selected from the group consisting of:
    (a) Fraction No. 3 obtained by extracting bovine pineal glands at a cold temperature by homogenizing said pineal glands in approximately 95% ethanol, stirring for a period of time to essentially complete the extraction, centrifuging, separating said centrifugate and stirring same at a cold temperature for a period of time to essentially complete the extraction in approximately 50% ethanol, centrifuging, separating said centrifugate and stirring same for a period of time in 4M guanidine hydrochloride to essentially complete the extraction, centrifuging, separating said resultant supernate, dialyzing said supernate against water, centtrifuging, separating said result supernate and lyophilizing same to dryness thereby obtaining the desired composition;
    (b) Fraction No. 4 obtained by extracting pineal bovine glands at a cold temperature by homogenizing said pineal glands in approximately 95% ethanol, stirring for a period of time to essentially complete the extraction, centrifuging, separating said centrifugate and stirring same for a period of time to essentially complete the extraction in approximately 50% ethanol, centrifuging, separating said centrifugate and stirring same for a period of time in 4M guanidine hydrochloride to essentially complete the extraction, centrifuging, separating said resultant supernate, dialyzing said supernate against water, centrifuging, separating said resultant centrifugate, and lyophilizing and resultant centrifugate, and lyophilizing same to dryness thereby obtaining the desired composition;
    (c) Fraction No. 5 obtained by extracting bovine pineal glands at a cold temperature by homogenizing said pineal glands in approximately 95% ethanol, stirring for a period of time to essentially complete the extraction, centrifuging, separating said centrifugate and stirring same for a period of time to essentially complete the extraction in approximately 50% ethanol, centrifuging, separating and centrifugate and stirring same for a period of time in 4M guanidine hydrochloride to essentially complete the extraction, centrifuging, separating said resultant centrifugate and lyophilizing same to dryness thereby obtaining the desired composition; and mixtures thereof.
and a cosmetic carrier for topical application to the skin in solid or liquid form either singularly or in combination thereof in various bases 12. A composition according to claim 11 wherein said period of stirring is overnight.

13. A composition according to claim 12 wherein said cold temperature of extraction is approximately 4° C.

14. A composition according to claim 13 wherein said homogenizing is done on ice.

15. A composition according to claim 14 wherein the composition is Fraction No. 3.

16. A composition according to claim 14 wherein the composition is Fraction No. 4.

17. A composition according to claim 14 wherein the composition is Fraction No. 5.

18. A method for the maintenance of and improvement of skin structure and texture of human skin comprising, administering topically to skin 1 µg to 100 mg of dry bovine pineal, glands extract material per ml or cc of cosmetically acceptable liquid solution selected from the group consisting of Fraction No. 3, Fraction No. 4, and Fraction No. 5, or mixtures thereof.

* * * * *